CHRYSANTHEMUM PLANT
Filed March 7, 1974
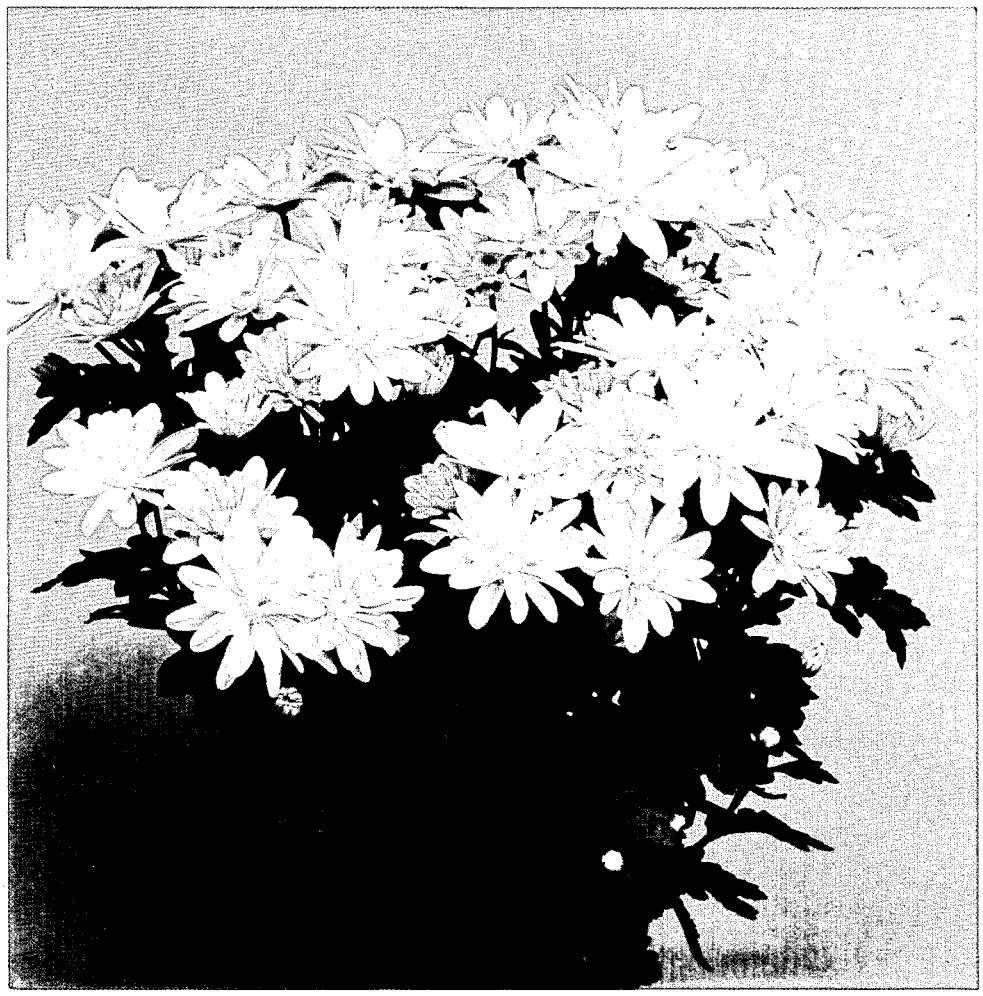

United States Patent

Plant Pat. 3,740

Patented July 8, 1975

3,740
CHRYSANTHEMUM PLANT

Walter H. Jessel, Jr., Doylestown, and William E. Duffett, Akron, Ohio, assignors to Yoder Brothers, Inc., Barberton, Ohio

Filed Mar. 7, 1974, Ser. No. 449,069
Int. Cl. A01h *5/00*
U.S. Cl. Plt.—74 1 Claim

The present invention comprises a new and distinct cultivar of chrysanthemum plant known by the varietal name Gem which is a seedling of #67079–001, self-pollinated. The parent is known commercially by the varietal name Dramatic and is disclosed in U.S. Plant Pat. 3,189, and is identified for breeding purposes by the above breeding number.

The new cultivar is similar in many respects to Dramatic, having the same characteristics of:

1. Flower form and size.
2. General growth habit, both as a cut spray and as a pot.
3. General foliage characteristics, including size, color and texture.
4. Approximately equal height in pot mum programs when given one to two weeks of long days as defined in the timetables of Yoder Brothers, Inc., Barberton, Ohio, for the various recommended seasons and given two 2500 p.p.m. applications of the growth regulator B–9.

The new cultivar is distinguished from Dramatic by the following characteristics, when grown under comparable conditions:

1. Approximately one week earlier flowering response.
2. Four to eight days increased permanence due to improved form and color retention.
3. Approximately 8″–9″ greater height in cut spray programs given 2–3 weeks of long days.
4. A lavender flower color.
5. A purple dot in the center of the disc which disappears as the flower matures.

The new cultivar was selected from the progeny of the designated cross, and when asexually reproduced by cuttings at Barberton, Ohio, has been found to retain its distinctive characteristics through successive propagation.

Our new cultivar, when grown in the vicinity of Barberton, Ohio, has a response period of approximately 7 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the Northern United States is from May through October, and in the Southeastern United States, Southwestern United States, coastal California, and southern Florida under outdoor conditions, from November through April.

The accompanying color photographic drawing shows the unique characteristics of the new cultivar, with the color being as nearly true as possible with color illustrations of this type.

In the following description, color references are made to the Munsell Limit Color Cascade, 1972 edition (designated MLCC), and the Munsell Book of Color, 1963 edition (designated MBC), and comparisons are made with the cultivar Dramatic. Where only a single value or description appears for the new cultivar, the same value or description applies as well to the parent cultivar Dramatic.

Botanical Classification.—*Chrysanthemum morifolium*

| | Gem | Dramatic |
|---|---|---|
| Bloom: | | |
| Size | 2¾″ to 3¼″ | |
| Fully expanded | 3½″ | |
| Borne | In clusters of 7 to 8 on terminal sprays. | |
| Stems | Strong | |
| Form | Daisy (single) | |
| Permanence | 14–20 days | 10–12 days. |
| Color: | | |
| Center of flower. | Yellow-green, 5GY5/6 with a dot of purple, 5P2/8 to yellow, 6.25Y8.5/2 (MLCC). | Yellow-green, 5GY5/6 to yellow, 5Y8/14 (MBC). |
| Base of petals | Yellow-green, 5GY5/6 (MBC). | |
| Inside of petals. | Lavender pink, 0.1RP6.8/11.0 over light lavender pink, 3.0RP8.6/2.6 (MLCC). | Yellow-orange, 8.75YR7/12 to yellow, 5Y8/10 (MBC). |
| Reverse of petals. | do | Yellow, 5Y8/10 to light yellow, 5Y8.5/0 (MBC). |
| Tonality from a distance. | Light lavender pink | Golden bronze to amber yellow. |
| Discoloration | Lavender pink, 0.1RP6.8/11.0 over light lavender pink, 3.0RP8.6/2.6 (MLCC). | Yellow-bronze, 8.75YR7/12 to yellow, 5Y8/10 (MBC). |
| Petals: | | |
| Texture | Smooth | |
| Appearance and form. | Open at base, broad flat keel, tapering to a blunt 1–2 notched tip. | |
| Arrangement | Composite, whorled on a single receptable. | |
| Persistence | Resists shatter | |
| Fragrance | Typical chrysanthemum. | |
| Reproductive organs: | | |
| Stamen, anthers | 200+ | |
| Pollen | Abundant to none (functional sterility). | |
| Arrangement | Clustered in center of flower, if present. | |
| Styles | Present both ray and disc florets. | |
| Length | Short | |
| Ovaries | At the base of petal attached to receptacle. | |
| Plant: | | |
| Form | Herbaceous | |
| Growth | Upright | |
| Height: | | |
| Cut | Approximately 40″–45″ given 2–3 weeks of long days, and a total crop time of 9–10 weeks as defined in the timetables of Yoder Brothers, Inc., Barberton, Ohio, for the various recommended seasons. | Approximately 32″–36″ given 2–3 weeks of long days, and a total crop time of 11–12 weeks as defined in the timetables of Yoder Brothers, Inc., Barberton, Ohio, for the various recommended seasons. |
| Pot | Approximately 14″–18″ in a 4-cutting, 6″ pot, grown as a pinched spray pot and given 2 applications of B–9, and 7 week tall treatment (1–2 weeks of long days) as defined in the timetables of Yoder Brothers, Inc., Barberton, Ohio, for the various recommended seasons. | Approximately 14″–18″ in a 4-cutting, 6″ pot, grown as a pinched spray pot and given 2 applications of B–9, and 9 week tall treatment (1–2 weeks of long days) as defined in the timetables of Yoder Brothers, Inc., Barberton, Ohio, for the various recommended seasons. |

TABLE—Continued

| | Gem | Dramatic |
|---|---|---|
| Spread: | | |
| Cut | None grown single stem to slight when pinched. | |
| Pot | Approximately 9″–12″ in a 4-cutting, 6″ pot, grown as a pinched spray pot and given 2 applications of B-9 and 7 week tall treatment (1–2 weeks of long days) as defined in the timetables of Yoder Brothers, Inc., Barberton, Ohio, for the various recommended seasons. | Approximately 9″–12″ in a 4-cutting, 6″ pot, grown as a pinched spray pot and given 2 applications of B-9 and 9 week tall treatment (1–2 weeks of long days) as defined in the timetables of Yoder Brothers, Inc., Barberton, Ohio, for the various recommended seasons. |
| Foliage: | | |
| Top side | Dark green, 5.6GY2.3/3.6 (MLCC). | |
| Size | Length to width ratio 5:3 with length to 5″ and width to 3″. | Length to width ratio 11:6 with length to 5½″ and width to 3″. |
| Quantity | Numerous | |
| Shape | Spatulate lobed | |
| Ribs and veins | Prominent | |
| Edge | Moderately indented | |
| Serration | Coarse | |
| Under side | Greyed green, 7.5GY5/4 (MBC). | |
| Stipules | Very prominent | |

We claim:

1. A new and distinct cultivar of chrysanthemum capable of being grown in cut spray programs or as a pot mum and characterized particularly as to its uniqueness by its seven week response period; superior permanence of 14–20 days due to improved form and color retention; its 40″–45″ height in cut spray programs given 2–3 weeks of long days, and by its lavender flower color, with the flower having a purple dot in the center of the disc which disappears as the flower matures.

No references cited.

ROBERT E. BAGWILL, Primary Examiner